United States Patent [19]
Katto et al.

[11] Patent Number: 5,965,171
[45] Date of Patent: Oct. 12, 1999

[54] APPARATUS AND PROCESS FOR PRODUCING DENTURES HAVING SYNTHETIC RESIN BASE

[75] Inventors: Hiroyuki Katto, Neyagawa; Mitsuji Matsuyama, Daito, both of Japan

[73] Assignee: Satoyuki Matsushita, Takatsuji, Japan

[21] Appl. No.: 08/905,738

[22] Filed: Aug. 4, 1997

[30] Foreign Application Priority Data

Aug. 5, 1996 [JP] Japan .................................. 8-205756

[51] Int. Cl.⁶ .................................................. A61C 13/16
[52] U.S. Cl. ...................... 425/175; 249/54; 264/17; 264/39; 425/98; 425/178; 425/227; 425/DIG. 11
[58] Field of Search ............................ 249/54; 264/17, 264/39; 425/98, 175, 176, 178, 180, 227, DIG. 11

[56] References Cited

U.S. PATENT DOCUMENTS

| | | | |
|---|---|---|---|
| 3,368,244 | 2/1968 | Mueller | 425/175 |
| 3,607,996 | 9/1971 | Pickands | 425/98 |
| 3,663,141 | 5/1972 | Alain et al. | 425/175 |
| 3,762,848 | 10/1973 | Muller | 425/175 |
| 4,405,854 | 9/1983 | Lapointe | 425/176 |
| 4,472,342 | 9/1984 | Carr | 264/222 |

FOREIGN PATENT DOCUMENTS

| | | |
|---|---|---|
| B-61-9055 | 3/1986 | Japan . |
| 5-21919 | 3/1993 | Japan . |
| B-7-4395 | 1/1995 | Japan . |

*Primary Examiner*—James P. Mackey
*Attorney, Agent, or Firm*—Armstrong, Westerman Hattori, McLeland & Naughton

[57] ABSTRACT

An apparatus for producing dentures having a synthetic resin base comprises a flask tank provided with a tank closure which is opened when a flask is brought into and out of the tank and when resin is to be injected into the flask and which is closed when wax is to be removed. The flask tank has a wax pattern heater and is formed with fluid channels adapted to communicate with a resin injecting gate of the flask for successively supplying cleaning hot water, drying air and separating agent to the interior of the flask therethrough.

4 Claims, 5 Drawing Sheets

APPARATUS AND PROCESS FOR PRODUCING DENTURES HAVING SYNTHETIC RESIN BASE

BACKGROUND OF THE INVENTION

The present invention relates to an apparatus and a process for producing dentures having a synthetic resin base, and more particularly to an apparatus for producing such dentures which is adapted to execute all the steps of removing wax from a flask by heating a wax pattern therein, injecting and filling a synthetic resin into a pattern cavity formed by removing the wax and shaped in conformity with the denture, and polymerizing the filled resin, and to the process to be practiced by the apparatus.

In producing dentures having a synthetic resin base, it is common practice to use individual devices for performing the respective steps of removing wax from a flask by heating a wax pattern therein within a pot (see JP-B-4395/1995), injecting and filling a synthetic resin into the resulting pattern cavity (see Laid-Open Japanese Utility Model Application 21919/1993) and polymerizing the resin (see JP-B-4395/1995).

On the other hand, JP-B-9055/1986 discloses an apparatus for producing dentures having a synthetic resin base which comprises a set of devices for successively performing the three main steps, i.e., the steps of removing wax, injecting and filling synthetic resin, and polymerizing the resin. The production apparatus comprises in combination a portion for removing wax from a flask as placed in a flask tank using hot water, with a flask tank lid and a wax lid closed, a pressure device having a cylinder set in position with the tank lid closed and with the wax lid opened for injecting and filling a synthetic resin into the flask, and a portion for polymerizing the filled resin within the flask tank.

The flask for use in the production apparatus comprises two split segments which are prevented from separating from each other by being pressed against a side wall of the flask tank by a pressing device.

The conventional apparatus for producing dentures with a synthetic resin base has the following problems.

1. Since the flask is prevented from separating into the segments by being pressed against the flask tank wall by the pressing device, a strain is likely to occur in the resin if the flask is released from the pressing device before the resin is polymerized. Accordingly, when the flask filled with the resin is taken out from the tank and then heated for polymerization, impaired accuracy will result, so that the resin needs to be heated and polymerized within the flask tank with the flask held by the pressing device. Thus, the apparatus is not usable efficiently.

2. The apparatus requires two lids, i.e., the tank lid and the wax lid, and is therefore cumbersome and inefficient to operate.

3. If drops of cleaning water remain after cleaning the pattern cavity created by removing the wax, the presence of water impairs the quality and accuracy of resin filled in. When many flasks are used, the remaining water must be removed from all the flasks reliably during operation without forgetting or failure.

4. A separating agent needs to be applied to the pattern cavity reliably so as to render the filled resin readily removable from the flask after polymerization.

5. The production apparatus must be made compact and less susceptible to work errors to the greatest possible extent.

SUMMARY OF THE INVENTION

An object of the present invention is to provide an apparatus and a process which are free of all the foregoing problems and drawbacks for producing dentures having a synthetic resin base.

The present invention provides an apparatus for producing dentures having a synthetic resin base comprising a flask tank 20 having an open upper side for accommodating at least one flask 1, and an injection-filling device, the flask having a resin injecting gate 7 in an upper wall thereof and wax outlets 8 in a lower wall thereof, the flask tank 20 having a wax discharge bore 26 formed in a bottom wall thereof and adapted to communicate with the wax outlets 8 of the flask, the apparatus being operable to heat and melt a wax pattern 2 within the flask 1 as placed in the flask tank 20, remove wax from the flask 1 through the wax outlets 8 and the wax discharge bore 26, thereafter cause the injection-filling device to inject and fill a synthetic resin 43 from the resin injecting gate 7 into a pattern cavity 51 formed within the flask 1 by removing the wax, and polymerize the filled resin, the apparatus being characterized in that the flask tank 20 is provided with a tank closure 21 openable when the flask 1 is to be brought into and out of the flask tank 20 and when the resin is to be injected into the flask, the tank closure 21 being closable when the wax is to be removed, the flask tank 20 being provided with a wax pattern heating source 33, the tank closure 21 being formed with fluid channels 23, 24, 25 adapted to communicate with the resin injecting gate 7 of the flask 1 for successively supplying cleaning hot water, drying air and separating agent to the interior of the flask 1 therethrough.

With the production apparatus of the present invention, the flask 1 is placed into the flask tank 20, the tank closure 21 is then closed, the interior of the tank 20 is heated by the heating source 33, whereby the wax pattern 2 is melted for the removal of the wax. Cleaning hot water, drying air and separating agent are then successively supplied to the interior of the flask 1 via the fluid channels 23, 24, 25 of the closure 21 and via the resin injecting gate 7 of the flask 1. Thus, the step of cleaning and drying the pattern cavity required after removing the wax and the step of applying the separating agent needed before injecting and filling the resin can be performed automatically during sequential control of a series of steps without resorting to manual work. This eliminates the causes of faults that would occur if the operator forgets to perform one procedure or another as in handling many denture bases.

Preferably, the flask 1 comprises two split segments 1a, 1b fastened together with bolts 10 or like means, and the apparatus further comprises a polymerization heating plate 50 for heating the flask 1 as brought out of the flask tank after injection and filling. When the resin-filled flask as fastened is taken out from the tank and then heated for polymerization by a single-side polymerization method, the above feature eliminates the likelihood of strain occurring in the resin. Consequently, the desired resin-base denture can be obtained with high accuracy. Moreover, while a plurality of flasks are heated for polymerization, another group of flasks can be placed into the flask tank for the removal of wax and the injection of resin. The production apparatus is therefore usable with improved efficiency.

Preferably, the injection-filling device comprises a pressure unit 45 settable at a variable pressure, a cylinder 40 having a bottom and charged with dissolved or melted synthetic resin 43, and a resin pressing plate 44 provided at a lower end of a pressure rod 46 movable upward and downward by the pressure unit 45 for downwardly pressing the resin 43 within the cylinder 40, a fitting projection 52 being formed on one of the bottom of the cylinder 40 and the upper wall of the flask 1, a fitting recess 9 being formed in the other of the bottom and the upper wall. The cylinder 40 can then be positioned in place readily relative to the flask 1 for the injection-filling step.

Preferably, the apparatus comprises a device for opening and closing the tank closure 21, the closure opening-closing device comprising a lever 34 having a horizontal pivot 38 positioned to the rear of an upper rear edge of the flask tank 20, a base-end pulley 35 mounted on the pivot 38 concentrically therewith, a forward-end pulley 36 rotatably mounted on a forward end of the lever 34, and a belt 37 reeved around the two pulleys 35, 36, the forward-end pulley 36 being secured to the tank closure 21, so that when the lever 34 moves counterclockwise through a required angle from a horizontal position toward a vertical position to open the tank closure 21, the forward-end pulley 36 rotates clockwise through approximately the same angle as the lever to open the tank closure 21 while gradually moving the tank closure 21 from a horizontal position toward a vertical position. The space S required for opening and closing the tank closure 21 is then defined by a horizontal plane and a vertical plane which extend through the axis of the pivot 38 of the lever 34, and a plane 39 which is curved inward toward the pivot 38 of the lever 34. The space is much smaller than in the conventional apparatus, permitting the pressure unit 45, etc. to be readily arranged above the flask tank 20.

The present invention provides a process for producing dentures having a synthetic resin base comprising the steps of removing wax by placing a flask 1 having a resin injecting gate 7 in an upper wall thereof and wax outlets 8 in a lower wall thereof into a flask tank 20 having an open upper side, heating and melting a wax pattern 2 within the flask 1 and discharging the wax through a wax discharge bore 26 formed in a bottom wall of the flask tank 20 and communicating with the wax outlets 8 of the flask; thereafter injecting and filling a synthetic resin 43 from the resin injecting gate 7 into a pattern cavity 51 formed within the flask 1 by removing the wax; and polymerizing the filled resin, the process being characterized by injecting cleaning hot water into the flask 1 through fluid channels 23, 24, 25 formed in a tank closure 21 and through the resin injecting gate 7 of the flask 1 after the wax pattern 2 is almost completely melted and discharging the water through the wax discharge bore 26 to form the pattern cavity 51 within the flask 1 in the wax removing step, and subsequently supplying drying air to the pattern cavity 51 through the fluid channels 23, 24, 25 and the resin injecting gate 7 to remove the water from the interior of the pattern cavity 51.

With the process of the invention, the removal of wax is automatically followed by cleaning and drying without resorting to manual work. This reliably prevents drops of the cleaning water from remaining in the pattern cavity formed within the flask, obviating the likelihood of the filled resin becoming degraded and impaired in accuracy.

Preferably, a plug 28 in the bottom wall of the flask tank 20 is closed by a plug operating mechanism 30 after the wax removing step, followed by pouring of a separating agent into the pattern cavity 51 through the fluid channels 23, 24, 25 and the resin injecting gate 7 and then by opening of the plug 28 by the plug operating mechanism 30 to discharge an excess of the separating agent. Thus, the removal of wax is automatically followed by the application of separating agent as required before the injection of resin without resorting to manual work, so that the separating agent can be reliably applied to the pattern cavity 51 to facilitate removal of the filled resin on curing.

Preferably in the resin filling step, dissolved or melted synthetic resin 43 is charged into a cylinder 40 having a resin injection opening 41 in a bottom wall thereof after the wax discharge bore 26 is closed with a plug 28, and injected and filled into the pattern cavity 51 by applying pressure to the resin 43 with a pressure rod 46 of a pressure unit 45 set at an injection pressure through a resin pressing plate 44, with the injection opening 41 registered with the resin injecting gate 7 of the flask 1, and the pressure of the pressure unit 45 is altered to a holding pressure after the resin is completely filled in. The alteration of the pressure to be applied by the pressure unit to an appropriate holding pressure serves to eliminate internal strain. Preferably, the holding pressure is in the range of ½ to ¹⁄₁₀ of the maximum static pressure of the pressure unit.

Preferably, two split segments 1a, 1b are fastened together by bolts 10 or like means to form the flask 1 before the wax removing step, and the polymerizing step is performed by a single-side polymerization method wherein the flask 1 as brought out of the flask tank 20 in the fastened state is placed on a polymerization heating plate 50, with an outer side 1c of the flask closer to the mucosal side of a resin base in contact with the plate 50 so that polymerization proceeds from the mucosal side of the base in contact with the alveolar ridge and required to have an accurate finish. No strain then occurs in the resin when the flask 1 is taken out from the flask tank after the injection of the resin, consequently affording a highly accurate resin-base denture. Moreover, an improved production efficiency will result since the polymerization step can be performed concurrently with the wax removing step and the injection-filling step.

DESCRIPTION OF THE PREFERRED EMBODIMENTS

Embodiments of the invention will be described below with reference to the drawings. The terms "front" and "rear" herein used refer respectively to the right-hand side and left-hand side of FIG. 5. The terms "clockwise" and "counterclockwise" are used with reference to FIG. 5.

Figure 1:
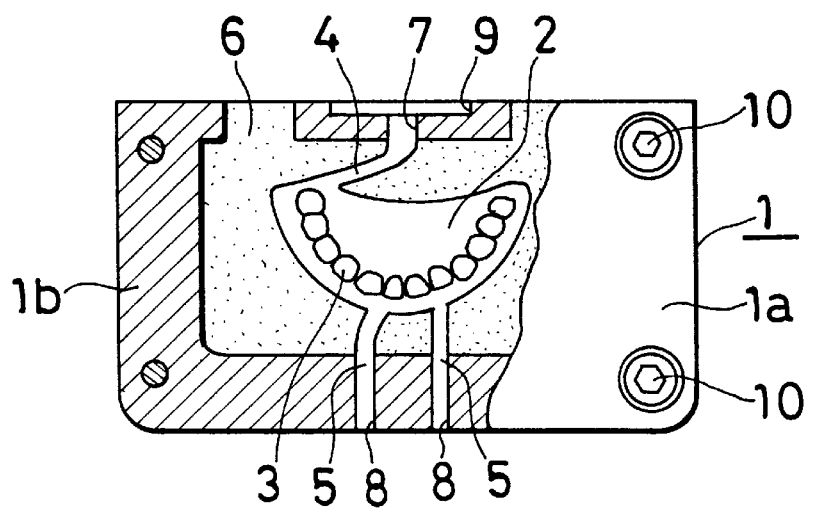
FIG. 1 is a sectional view showing a flask for use in the apparatus and process of the invention for producing dentures having a synthetic resin base.

With reference to FIG. 1 showing a flask 1 for use in an apparatus and a process for producing dentures having a synthetic resin base according to the invention, the flask 1 is in the form of a rectangular parallelepipedal body comprising two split segments 1a, 1b. Provided in the interior of the flask body are a denture base wax pattern 2, artificial teeth 3 mounted on the wax pattern 2 and an embedding agent 6, such as plaster, enclosing the wax pattern 2. A resin injecting gate 7 is formed in the upper wall of the flask 1, and wax outlets 8 in the bottom wall of the flask 1. A wax sprue 4 is provided between the gate 7 and the wax pattern 2, and wax vents 5 between the wax pattern 2 and the wax outlets 8. Formed in the upper wall of the flask 1 is a fitting recess 9 serving to position a cylinder in place in the resin injection-filling step to be described later. The recess 9 is circular when seen from above, and the gate 7 is positioned approximately in the center of the bottom of the recessed portion. The two segments 1a and 1b of the flask body are fastened together with means such as bolts 10.

Figure 2:
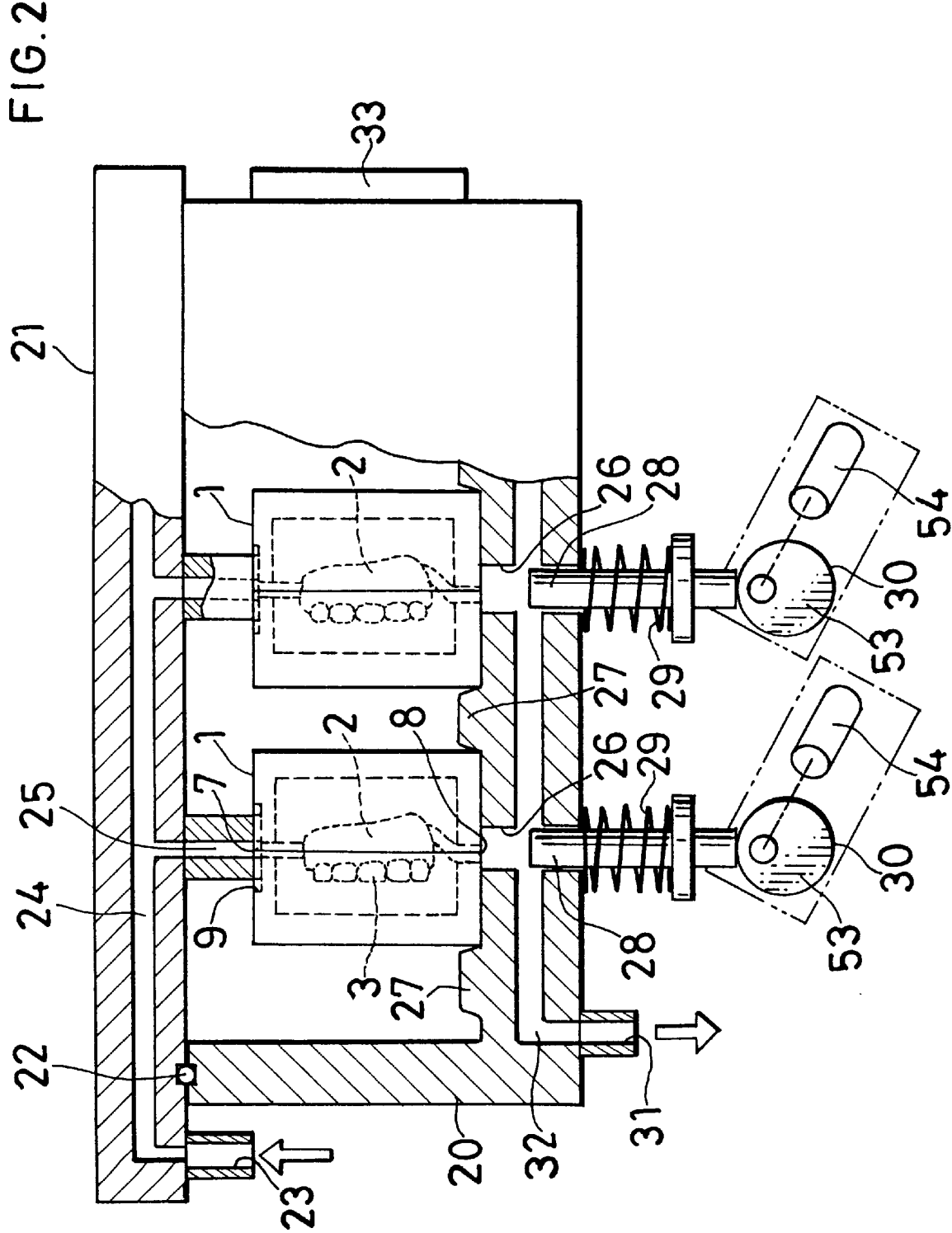
FIG. 2 is a sectional view showing the wax removing step of the process to be performed by the apparatus.

FIG. 2 shows a flask tank 20 and a tank closure 21 for use in the apparatus and process of the invention for producing synthetic resin-base dentures. The drawing shows the tank and closure in the step of removing the wax.

The flask tank 20 is adapted to accommodate a plurality of flasks 1 at the same time for treatment, and provided with a heating source 33 such as an electric heater for heating the flasks 1.

The flask tank 20 has a bottom wall, which is formed with wax discharge bores 26 each in communication with the wax outlets 8 of each flask 1 when flasks 1 are placed in, a fluid discharge channel 32 communicating with the wax bores 26 for discharging molten wax and other fluids therethrough via a spout 31 provided on the lower surface of the bottom wall, and guides 27 for positioning the flasks 1 in place with their wax outlets 8 in register with the respective wax discharge bores 26. The guides 27 extend from the front rearward and are trapezoidal in cross section. One pair of guides 27 are arranged in the form of ridges at opposite sides of the inner surface portion of the bottom wall for placing each flask 1 thereon. The wax discharge bore 26 is closed with a plug 28 which is movable upward and downward by a plug operating mechanism 30. The wax removing step is performed with the wax discharge bores 26 open, and the injection-filling step with the wax discharge bores 26 closed.

The plug operating mechanism 30 comprises a disklike eccentric cam 53 movable from below into contact with the plug 28 which is biased downward by a spring 29. The cam 53 has an eccentric shaft, which is rotated by a motor 54 to thereby move the plug 28 upward and downward.

The tank closure 21 is provided over the flask tank 20 fluidtightly with a packing 22 interposed therebetween. The closure 21 is formed with downward vertical channels 25 communicating with the resin injecting gates 7 of the respective flasks 1 when the closure is closed, a horizontal channel 24 communicating with the downward vertical channels 25 and an upward vertical channel 23 communicating with the horizontal channel 24. The downward vertical channel 25 has a leakproof structure including a packing. Through these fluid channels 23, 24, 25, cleaning hot water, drying air and separating agent are successively supplied to the flasks 1.

Figure 3:
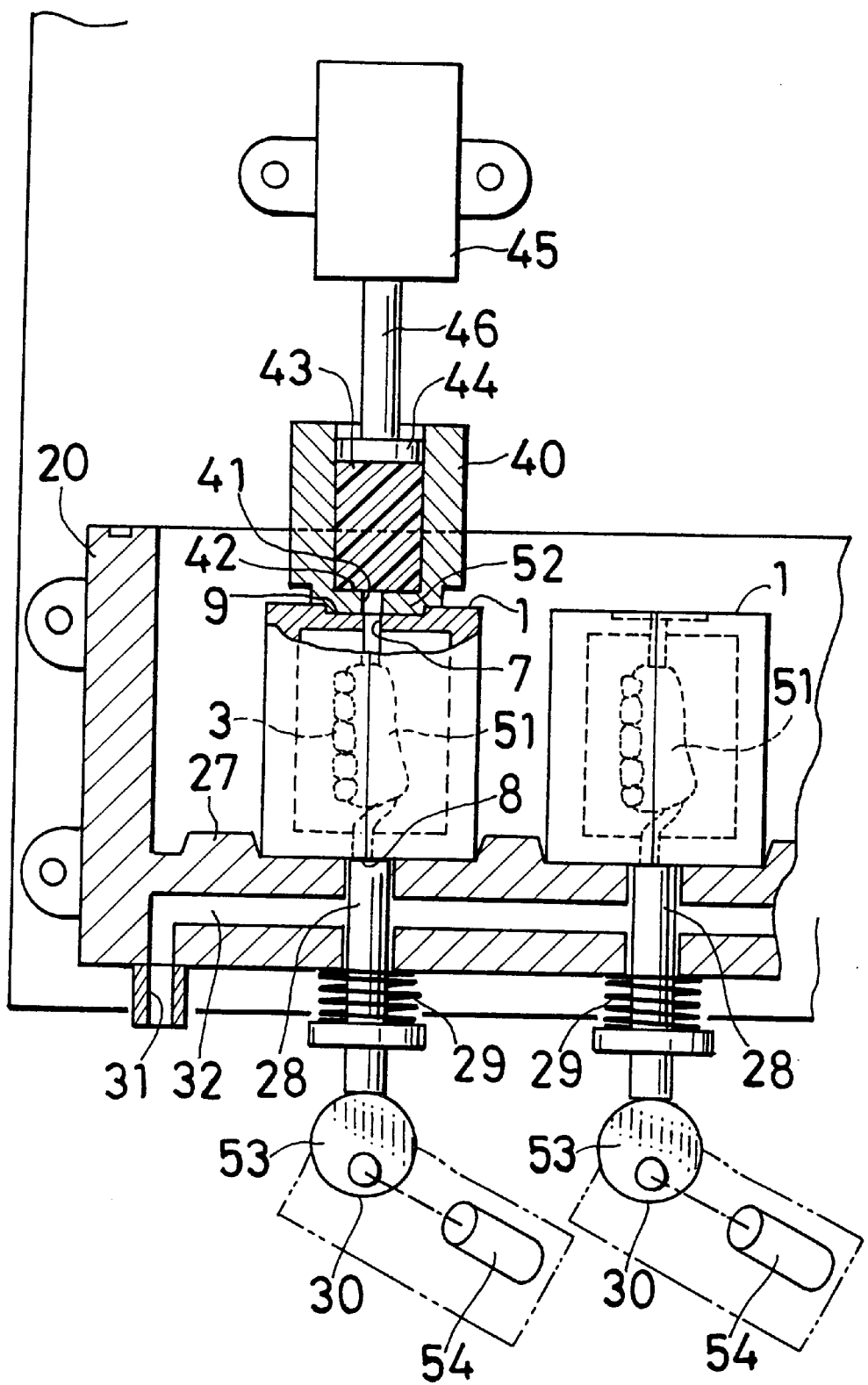
FIG. 3 is a sectional view of the resin filling step to be performed by the apparatus.

FIG. 3 shows an injection-filling device for use in the apparatus of the invention for producing synthetic resin-base dentures.

The injection-filling device, which is provided above each of the flasks 1, comprises a pressure unit 45, a hollow cylinder 40 having a bottom and filled with a dissolved or molten synthetic resin 43, a pressure rod 46 movable upward and downward by the pressure unit 45, and a resin pressing plate 44 provided at the lower end of the pressure rod 46 for downwardly pressing the resin 43 within the cylinder 40.

The pressure device 45, typical of which is a hydraulic device, is settable at a variable pressure and operates for injecting and pressurizing the resin and subsequently applying a protective pressure.

The bottom wall of the cylinder 40 has a slightly reduced diameter and is formed on its lower surface with a fitting projection 52 projecting downward and having a circular cross section. The projection 52 is snugly fittable into the recess 9 in the upper wall of the flask 1. With the projection 52 snugly fitting in the recess 9, an injection opening 41 formed in the bottom wall of the cylinder 40 is in register with the resin injecting gate 7 of the flask 1. The resin pressing plate 44 is in the form of a disk having an outside diameter equal to the inside diameter of the cylinder 40 and is moved down by the pressure rod 46, pressing the synthetic resin 43 while confining the resin 43 in the cylinder, whereby a pattern cavity 51 is progressively filled with the resin 43. Indicated at 42 is diaphragm at the bottom of the mass of resin. The fitting projection 52 and recess 9 need not always be circular in cross section but can be of rectangular cross section or shaped otherwise.

Figure 4:
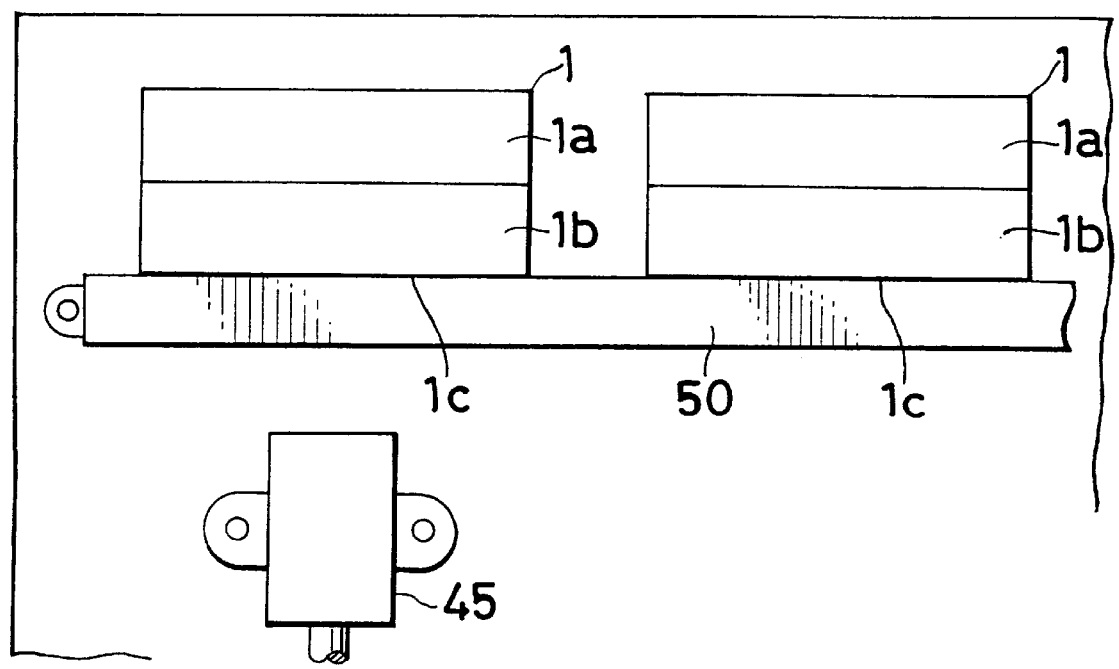
FIG. 4 is a sectional view showing the polymerization step of the process to be performed by the apparatus.

FIG. 4 shows a polymerization device for use in the apparatus and process of the invention for producing resin-base dentures.

The polymerization device has a heating plate 50 disposed above the pressure unit 45 for heating the resin for polymerization. The resin can be heated at a predetermined proper temperature by the heating plate 50 for a specified period of time, the heating temperature and time being dependent on the type of resin. On completion of the resin injection step, the flasks 1 are taken out from the flask tank 20, placed on the heating plate 50 and thereby polymerized.

Figure 5:
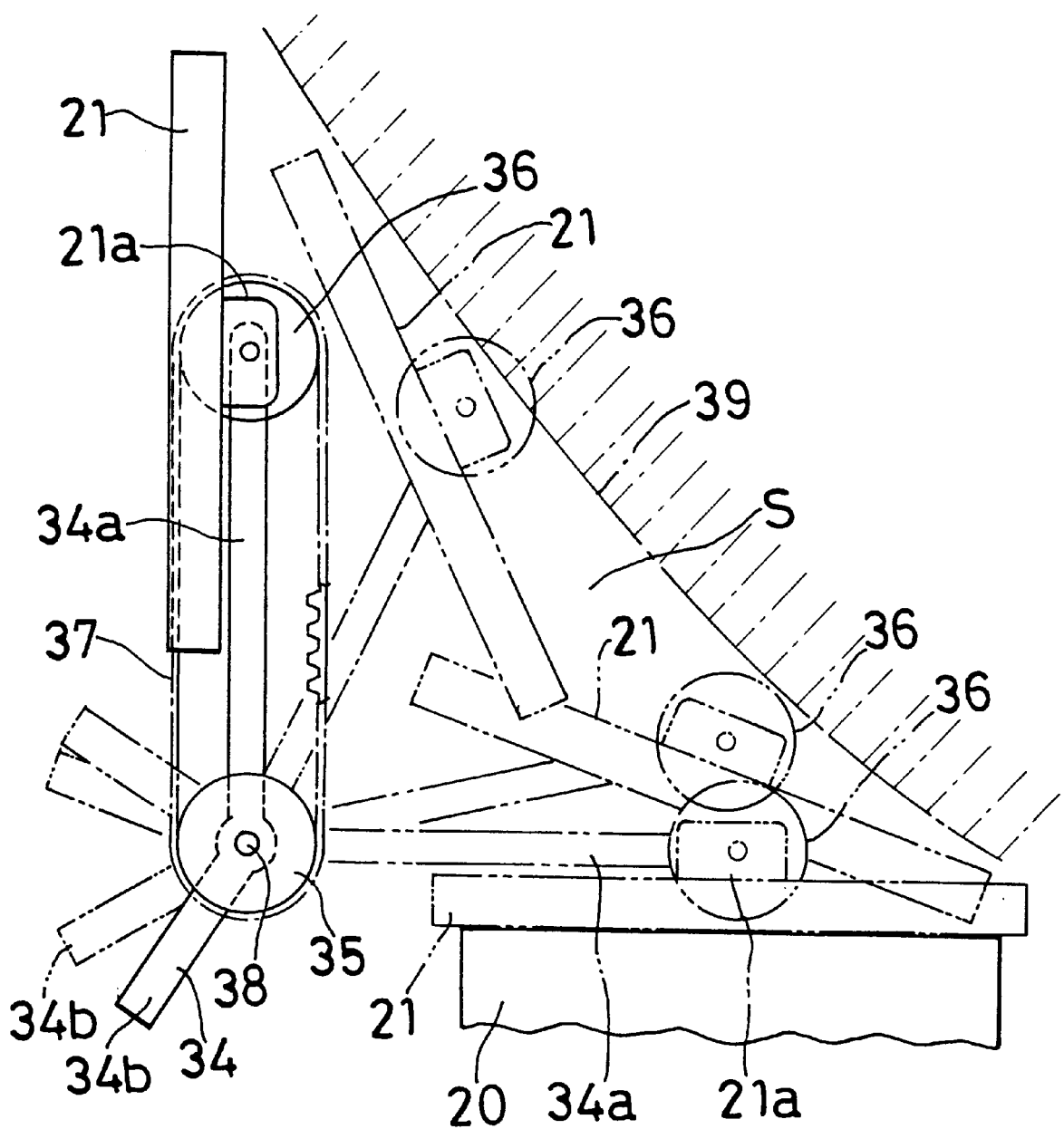
FIG. 5 is a side elevation showing a closure opening-closing device included in the apparatus.

FIG. 5 shows a tank closure opening-closing device for use in the apparatus and process of the invention for producing dentures with a synthetic resin base.

The flask tank closure 21 is closed when the wax is to be melted out, and is opened and held in a vertical position when the flasks are to be placed in and taken out and when the resin is to be injected.

The tank closure opening-closing device comprises a lever 34 movable about a horizontal pivot 38 positioned to the rear of the upper rear edge of the flask tank 20. The lever 34 comprises a long portion 34a which is in a horizontal position when the tank closure 21 is closed and assumes a vertical position as pivotally moved counterclockwise through 90 deg from the horizontal position when the closure 21 is opened, and a short portion 34b integral with the base end of the long portion 34a and bent at an angle therewith. The horizontal pivot 38 is located at the junction of the long portion 34a and the short portion 34b. When the short portion 34b is so driven as to turn counterclockwise, the long portion 34a is turned counterclockwise.

The long portion 34a of the lever 34 has a pulley 35 at its base end and a pulley 36 at its forward end. A belt 37 is reeved around the two pulleys 35, 36. The tank closure 21 is provided at the midportion between the front and rear end thereof with an upward projection 21a which is secured to the forward-end pulley 36. When the base-end pulley 35 is rotated clockwise by a motor (not shown), the forward-end pulley 36 rotates clockwise, pivotally moving the tank closure 21 clockwise. The lever 34 and the tank closure 21 are so timed that the angle of pivotal movement of the lever 34 is equal to the angle of pivotal movement of the closure 21 (angle of rotation of the pulleys 35, 36).

To open the tank closure 21, therefore, the lever 34 is moved counterclockwise through 90 deg from horizontal position toward vertical position. With this movement, the forward-end pulley 36 is rotated clockwise through approximately the same angle as above to gradually move the closure 21 from horizontal position toward vertical position for opening. The angle through which the lever 34 is pivotally moved is not limited exactly to 90 deg but can be a smaller angle. The position of the tank closure 21 as opened is then inclined from the vertical.

Figure 6:
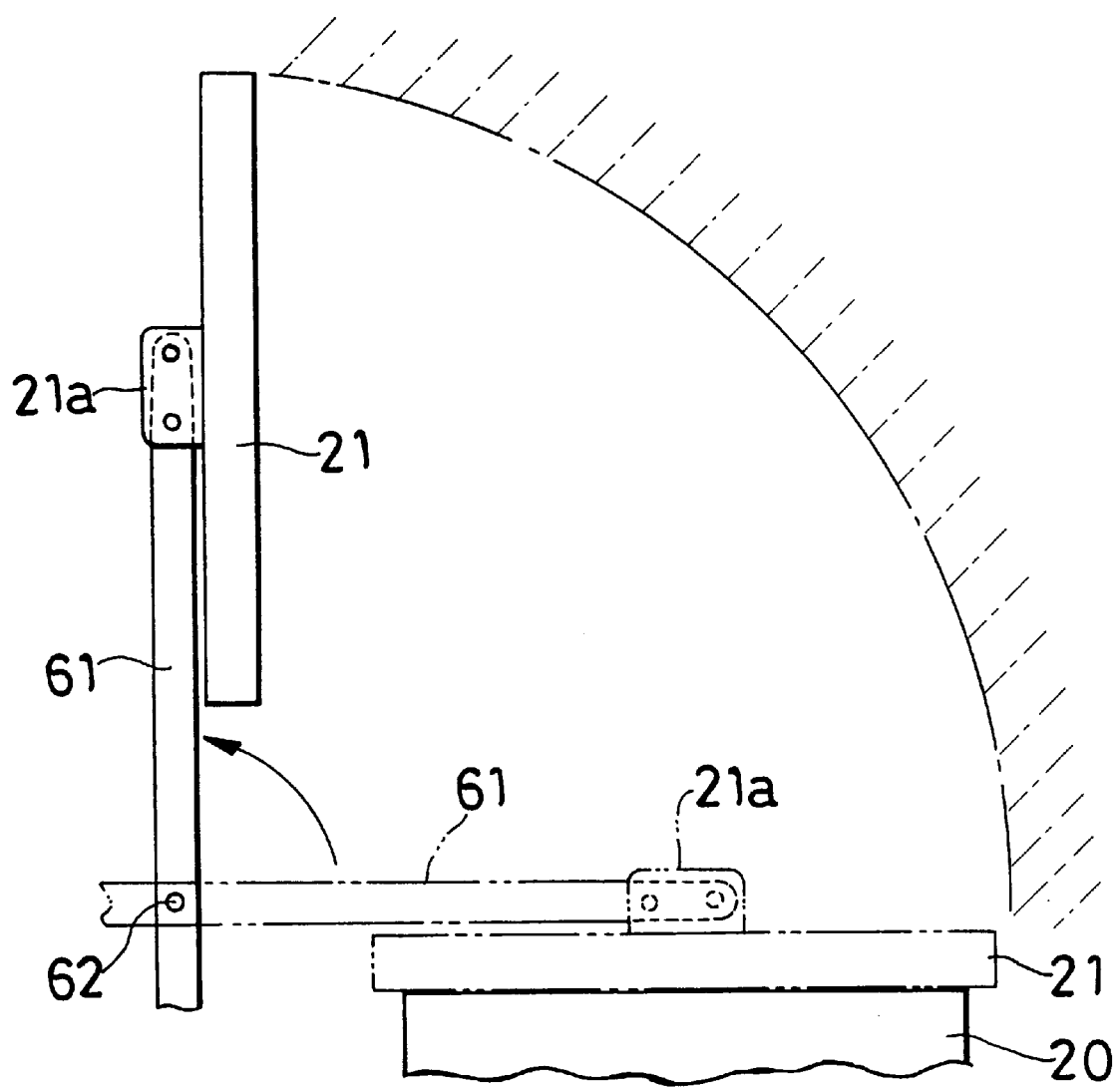
FIG. 6 is a side elevation showing a closure opening-closing device included in a conventional apparatus for producing synthetic resin-base dentures.

FIG. 6 shows a conventional tank closure opening-closing device, which comprises a lever 61 movable about a horizontal pivot 62 positioned to the rear of the upper rear edge of a flask tank 20. The lever 61 assuming a horizontal position when the tank closure 21 is in its closed state is pivotally moved counterclockwise through 90 deg from this position to a vertical position to open the closure 21. The tank closure 21 is fixed to the forward end of the lever 61. Accordingly, the closure 21 is opened and closed by performing a quarter of circular motion about the horizontal pivot 62. The space through which the closure 21 moves at this time is a quarter of circular area shown in FIG. 6. Since no other device can be installed in this space for the movement of the tank closure 21, compacting the apparatus for producing resin-base dentures requires diminution of this space.

With the tank closure opening-closing device of the invention shown in FIG. 5, on the other hand, the space S required for opening and closing the closure 21 is defined by a horizontal plane and a vertical plane which extend through the axis of the pivot 38 of the lever 34, and a plane 39 inwardly curved toward the pivot 38, and is much smaller than in the conventional device. The pressure units 45, etc. can therefore be readily arranged above the flask tank 20.

A description will be given below of the process for producing synthetic resin-base dentures, using the foregoing apparatus.

1. Wax Pattern Placing Step

First, a set of artificial teeth 3, a denture base wax pattern 2, a pin for forming the wax sprue 4, and members for forming the wax vents 5 are placed in the conventional manner into each of flasks 1 comprising the segments 1a, 1b. The segments 1a, 1b are fastened together with the bolts 10, and plaster or like embedding agent 6 is packed into the flask.

2. Wax Removing Step

The flasks 1 are then placed into the flask tank 20, as positioned in place by the guides 27. Each flask 1 is heated by the heating source 33 to melt the wax of the wax pattern 2 within the flask 1. After the wax is almost completely melted, cleaning hot water is injected into the tank through the fluid channels 23, 24, 25 of the tank closure 21, whereby the wax of the wax pattern 2 within the flask 1 is caused to flow out from the flask 1 through the wax outlets 8, passed through the opened wax discharge bore 26 of the tank 20 and run off from the spout 31 of the tank 20 via the fluid discharge channel 32 along with the flow of hot water. Consequently, the interior of the flask 1 is cleaned to form a pattern cavity 51.

Since the bottom wall of the flask tank 20 is formed with the guides 27 for positioning the flasks 1, each flask 1 can be held within the tank 20 in this step, as accurately positioned in place. As a result, the wax outlets 8 are registered with the wax discharge bore 26, and the downward vertical channel 25 communicating with the channels 23, 24 is registered with the resin injecting gate 7 of the flask 1. The cleaning hot water can therefore be introduced into the flask 1 through the fluid channels 23, 24, 25.

3. Removal of Remaining Water from the Pattern Cavity 51 and Injection of Separating Agent Subsequently, drying air is admitted through the same fluid channels 23, 24, 25 to remove the remaining water from each pattern cavity 51. This reliably obviates the likelihood of drops of cleaning water remaining within the pattern cavity 51 after the cavity is formed, precluding the degradation of the resin to be filled and the impairment of accuracy of resin molding to be obtained. The plug operating mechanism 30 is thereafter actuated to close the plug 28 at the bottom of the flask tank 20, a separating agent for rendering the molded resin smoothly releasable from the flask is injected through the fluid channels 23, 24, 25, and the plug 28 is then opened by the mechanism 30 to draw off an excess of the separating agent, whereby the separating agent can be reliably applied to the pattern cavity 51 for the separation of the resin from the flask, ensuring facilitated removal of the resin from the flask on polymerization.

The steps 2 and 3 described are included in a series of steps to be controlled sequentially and can be executed automatically without resorting to manual work. This eliminates the causes of faults that could occur if the operator forgets to perform one procedure or another while handling many flasks for preparing denture bases. Furthermore, the production apparatus can be compact since the cleaning hot water, drying air and separating agent are all supplied and drawn off through the same channels.

4. Opening the Flask Tank Closure

The closure is opened in the manner already described before the resin is filled into each flask.

5. Resin Filling Step

The pressure rod 46 of the pressure unit 45 set at the desired injection pressure applies pressure through the resin pressing plate 44 to dissolved or melted synthetic resin 43 filled in the cylinder 40, injecting the resin 43 into the pattern cavity 51 within the flask 1. When the resin is completely filled in, the pressure to be applied by the pressure unit 45 is altered to a holding pressure.

If the filled resin is held pressed under the initial injection pressure, an excessive pressure will act on the resin in the interior of the pattern cavity 51, producing a residual stress to result in internal strain to entail undesirable molding strain.

After the completion of filling, the pressure setting of the pressure unit 45 is altered to the holding pressure which produces no internal strain, using engineering means such as a sensor for detecting increases of pressure. Preferably, the holding pressure is in the range of ½ to ⅒ of the maximum static pressure of the pressure unit 45. When such pressure is applied, the resin completely molded provides a denture base which is diminished in strain.

6. Polymerization Step

After the completion of filling, each flask 1 is taken out as fastened from the flask tank 20. Since the mucosal side of the resin base in contact with alveolar ridges (dental necks) especially needs to be finished with high accuracy, the flask 1 is placed on the heating plate 50 with the outer side 1c thereof closer to the mucosal side in contact therewith to practice a single-side polymerization method so that the polymerization will proceed from the mucosal side.

This step not only affords resin-base dentures with high accuracy but also makes it possible to place another group of flasks into the flask tank for the removal of wax and the injection of resin, consequently rendering the apparatus usable with an improved efficiency. The flasks as accommodated in the flask tank can of course be subjected to the polymerization step with use of the heating source of the tank when so desired.

To describe the efficiency of the foregoing apparatus numerically, the apparatus requires about 20 minutes for the wax removing-cleaning step, several minutes for the resin injection-filling step and about 30 minutes for the polymerization step (exclusive of cooling time). The polymerization step conducted without using the flask tank reduces the production cycle of the present apparatus to ½, making the apparatus useable with a doubled efficiency.

The apparatus and process of the invention comprises a plurality of block requirements, which need not always be fulfilled at the same time but may be met individually, or some them may be fulfilled in combination as will be apparent from the appended claims.

The present invention, although entitled "Apparatus and Process for Producing Dentures Having Synthetic Resin Base," is not limited to such dentures but is applicable also to the production of dentures made of synthetic resin.

What is claimed is:

1. An apparatus for producing dentures having a synthetic resin base comprising a flask tank 20 having an open upper side for accommodating at least one flask 1, and an injection-filling device, the flask having a resin injecting gate 7 in an upper wall thereof and wax outlets 8 in a lower wall thereof, the flask tank 20 having a wax discharge bore 26 formed in a bottom wall thereof and adapted to communicate with the wax outlets 8 of the flask, the apparatus being operable to heat and melt a wax pattern 2 within the flask 1 as placed in the flask tank 20, remove wax from the flask 1 through the wax outlets 8 and the wax discharge bore 26, thereafter cause the injection-filling device to inject and fill a synthetic resin 43 from the resin injecting gate 7 into a pattern cavity 51 formed within the flask 1 by removing the wax, and polymerize and cure the filled resin, the apparatus being characterized in that the flask tank 20 is provided with a tank closure 21 openable when the flask 1 is to be brought into and out of the flask tank 20 and when the resin is to be injected into the flask, the tank closure 21 being closable when the wax is to be removed, the flask tank 20 being provided with a wax pattern heating source 33, the tank closure 21 being formed with fluid channels 23, 24, 25 adapted to communicate with the resin injecting gate 7 of the flask 1 for successively supplying cleaning hot water, drying air and separating agent to the interior of the flask 1 therethrough.

2. An apparatus as defined in claim 1 which is characterized in that the flask 1 comprises two split segments 1a, 1b fastened together, the apparatus further comprising a polymerization heating plate 50 for heating the flask 1 as brought out of the flask tank after injection and filling.

3. An apparatus as defined in claim 1 or 2 which is characterized in that the injection-filling device comprises a pressure unit 45 settable at a variable pressure, a cylinder 40 having a bottom and charged with dissolved or melted synthetic resin 43, and a resin pressing plate 44 provided at a lower end of a pressure rod 46 movable upward and downward by the pressure unit 45 for downwardly pressing the resin 43 within the cylinder 40, a fitting projection 52 being formed on one of the bottom of the cylinder 40 and the upper wall of the flask 1, a fitting recess 9 being formed in the other of the bottom and the upper wall.

4. An apparatus as defined in claim 1 or 2 which is characterized in that the apparatus comprises a device for opening and closing the tank closure 21, the closure opening-closing device comprising a lever 34 having a horizontal pivot 38 positioned to the rear of an upper rear edge of the flask tank 20, a base-end pulley 35 mounted on the pivot 38 concentrically therewith, a forward-end pulley 36 rotatably mounted on a forward end of the lever 34, and a belt 37 reeved around the two pulleys 35, 36, the forward-end pulley 36 being secured to the tank closure 21, so that when the lever 34 moves counterclockwise through a required angle from a horizontal position toward a vertical position to open the tank closure 21, the forward-end pulley 36 rotates clockwise through approximately the same angle as the lever to open the tank closure 21 while gradually moving the tank closure 21 from a horizontal position toward a vertical position.

\* \* \* \* \*